United States Patent [19]

Tradowsky

[11] 4,026,024
[45] May 31, 1977

[54] VISE FOR TRANSFER OF CHECK-BITES

[76] Inventor: Michael Tradowsky, 10370 Blair Lane, Kirtland, Ohio 44094

[22] Filed: Oct. 20, 1975

[21] Appl. No.: 623,580

[52] U.S. Cl. .................................................. 32/19
[51] Int. Cl.² ......................................... A61C 9/00
[58] Field of Search ...................... 32/19, 20, 21, 32

[56] References Cited

UNITED STATES PATENTS

| | | | |
|---|---|---|---|
| 2,334,898 | 11/1943 | Bigger et al. | 32/19 |
| 2,554,277 | 5/1951 | Taylor, Jr. | 32/19 |

Primary Examiner—Robert Peshock
Attorney, Agent, or Firm—Donnelly, Maky, Renner & Otto

[57] ABSTRACT

A vise for transfer of check-bites characterized in that clutches fastened to the respective upper and lower arches of the patient's teeth or to the patient's alveolar ridges have screw-actuated vise means which, when loosened, enable protrusive and right and left excursions of the mandible, said vise means being tightened after each such excursion to lock the clutches in the respective check-bite positions for adjusting a dental articulator.

6 Claims, 7 Drawing Figures

U.S. Patent        May 31, 1977        4,026,024
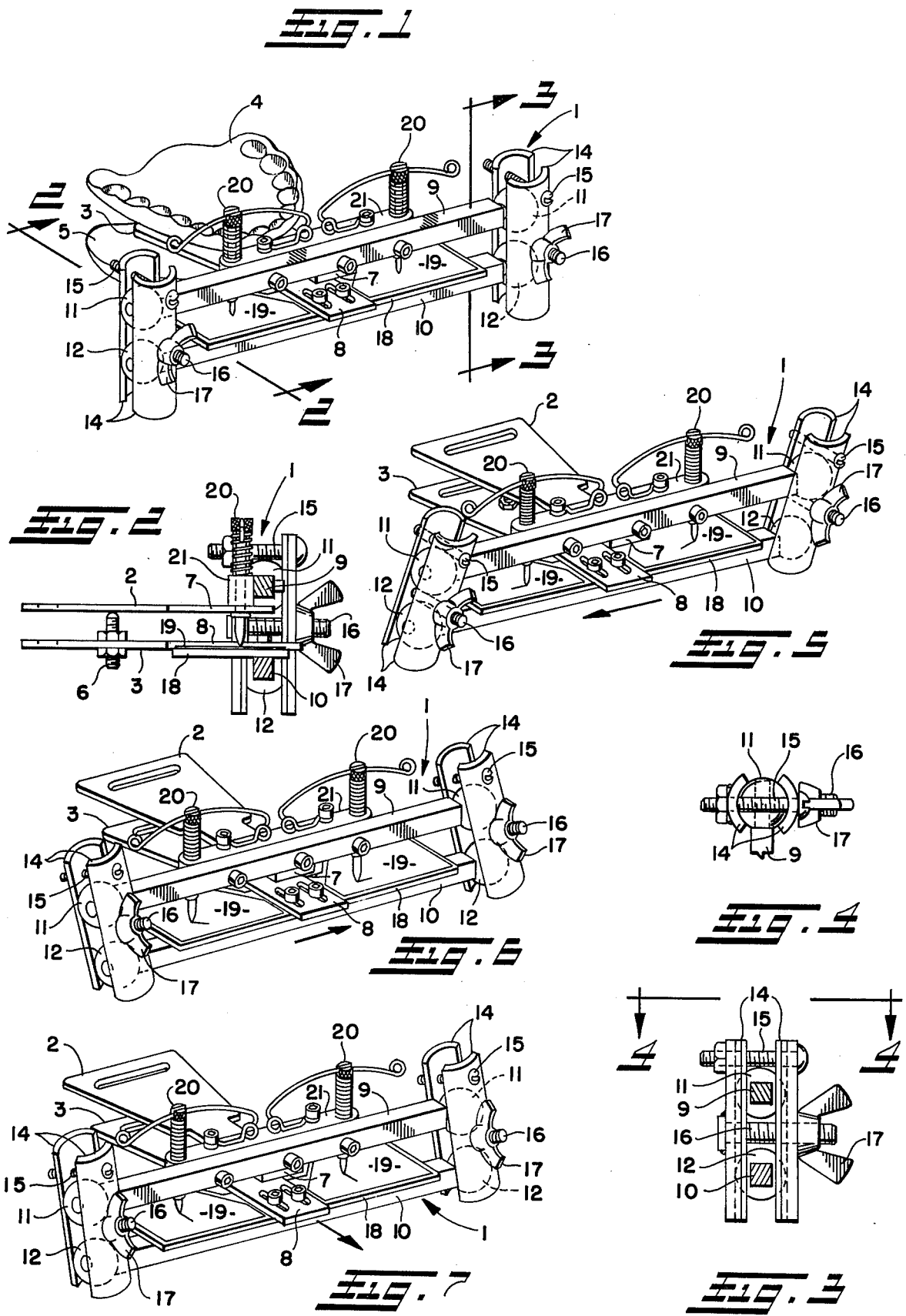

VISE FOR TRANSFER OF CHECK-BITES

BACKGROUND OF THE INVENTION

A prevalent practice in the taking of check-bites for use in adjusting a dental articulator involves fastening of clutches to the respective upper and lower arches of the patient's teeth or the patient's alveolar ridges. The clutches are secured to center bearing plates and are placed in the space between the tongue and the palate and are separated by a bearing stud. In order to get a reading of the jaw movements, the patient must hold his jaw in each position while fast-setting non-expandable stone is injected between the center bearing plates of the clutches. After the stone sets to fix the upper and lower clutches, the clutches are removed from the patient's mouth and placed between the models on the articulator for setting the articulator for the particular excursion. The stone is then removed and the center bearing plates cleaned for attaching the clutches in the patient's mouth to repeat the foregoing operation for the next excursion. As aforesaid, three check-bites are usually taken for adjusting the articulator i.e. one with the jaw moved to the right, one with the jaw moved to the left, and one with the jaw moved forward. To assist the patient in holding the jaw in the respective lateral check-bite positions while the injection stone is setting, the upper bearing plate will be formed with shallow depressions corresponding to the respective check-bite positions in which the rounded upper end of the bearing stud is engaged.

This method of fixing the clutches and center bearing plates by the use of stone has a number of disadvantages, namely, the mixing of the stone and the waiting for it to set in the mouth is time-consuming, the injecting of the stone between the center bearing plates without the patient moving the jaw is awkward, the patient has to hold perfectly still while the stone is setting and this may take several minutes for each check-bite, and the check-bite clutches and center bearing plates and mixing equipment have to be cleaned after each use. Furthermore, there is the added time and expense of forming the aforesaid shallow depressions in the upper bearing plate for each patient, and the added expense of replacement of upper bearing plates when the shallow depressions made for prior patients begin to interfere with the jaw excursions of a new patient.

SUMMARY OF THE INVENTION

In contradistinction to existing methods of taking check-bites for adjustment of a dental articulator for protrusive and right and left lateral jaw excursions, the device herein enables rapid and accurate fixing of the clutches and center bearing plates with respect to each other at each of the plurality of jaw positions simply by tightening the vise means thereof and immediately withdrawing the clutches from the patient's mouth for transfer to the articulator without the patient having to hold the jaw perfectly still for an extended period of time while the injected stone sets. After each adjustment of the articulator, the vise means may be loosened and the clutches fastened to the respective upper and lower arches of the patient's teeth or to the patient's alveolar ridges ready for the next excursion of the jaw and re-tightening of the vise means.

Other objects and advantages will appear from the ensuing description.

BRIEF DESCRIPTION OF THE DRAWING

FIG. 1 is a perspective view of a preferred form of vise for the transfer of check-bits showing the vise in the centric position of the jaws of the patient;

FIG. 2 is a cross-section view as viewed along the line 2—2, FIG. 1;

FIG. 3 is a cross-section view taken substantially along the line 3—3, FIG. 1;

FIG. 4 is a top plan view as viewed along the line 4—4, FIG. 3;

FIG. 5 illustrates the vise locked in the position which it assumes when the patient has made a right lateral excursion of the jaw;

FIG. 6 is the same as FIG. 5 except showing the locked position of the vise-after a left lateral excursion of the jaw; and FIG. 7 illustrates the vise as locked in position after protrusive excursion of the patient's jaw.

DETAILED DESCRIPTION OF A PREFERRED EMBODIMENT

The vise 1 herein disclosed comprises upper and lower center bearing plates 2 and 3 to which upper and lower plastic trays or clutches 4 and 5 are secured (see FIG. 1) in well known manner with the clutches 4 and 5 being fitted to the models of the patient's teeth to have a snug fit either with the patient's teeth or with the patient's alveolar ridges. The lower plate 3 has a center bearing stud 6. The narrow forwardly projecting portions 7 and 8 of the plates 2 and 3 are secured at the middle of the respective transverse bars 9 and 10 which have ball-shaped end portions 11;11 and 12;12 engaged between pairs of curved vise jaws 14 at the respective ends of said bars 9 and 10, the pairs of vise jaws 14 being retained between the screws 15 and 16 for universal movement. Upon tightening of the wing nuts 17, the pairs of balls 11;11 and 12;12 are frictionally gripping between the respective pairs of jaws 14 to lock the center bearing plates 2 and 3 in different relative positions for setting a dental articulator at each check-bite position. For example, FIG. 1 represents the centric bite position, FIG. 5 represents the check-bite position when the patient's jaw has been moved to the right (right lateral excursion), FIG. 6 represents the check-bite position when the patient's jaw has been moved to the left (left lateral excursion), and FIG. 7 represents the check-bite position when the patient's jaw has been moved forward (protrusive excursion). Each time that the vise 1 has been locked in the FIG. 1, 5, 6, and 7 positions, the setting at each position is transferred to a dental articulator for adjusting the latter in well known manner. The dental articulator may be of well known form such as disclosed in the U.S. Pat. No. 3,624,906 or one known as Simulator Model 2A manufactured by J. Aderer, Inc., 21–25 Forty-Fourth Avenue, Long Island City, N.Y. 11101.

The transverse bars 9 and 10 are adjustably secured with respect to the bearing plates 2 and 3 and in the case of the lower bearing plate 3, the attaching screws may also clamp on the lower bar 10 a tracing plate 18 which has tracing paper 19 secured thereto as by a pressure sensitive backing on the tracing paper 19 whereby the spring-loaded styli 20 will form traces on the paper 19 as shown. The upper plate 2 is adjustably secured to a stylus bar 21 and, in turn, the stylus bar 21 is secured as by screws to the upper bar 9 of the vise 1. In essence, the stylus 21 bar and tracing plate 18 assembly as secured to the respective bearing plates 2 and 3 may be of well known form such as the Aderer Simulator Minigraph with the tracings on paper 19 being used with the dental articulator as described above.

In summary therefore, it can be seen that several check-bites may be quickly made successively for transfer to the articulator without the disadvantages of the present practice of injecting fast setting non-expanding stone between the center-bearing plates 2 and 3 at each check-bite position, i.e. centric and protrusive, and right and left lateral excursions. Moreover, the upper bearing plate 2 herein need not have shallow depressions for seating of the rounded upper end of the bearing stud 6 in the respective right and left lateral excursions; and therefore, the time and expense of forming such depression is eliminated together with the expense of relatively frequent replacement of the upper bearing plate when prior depressions therein interfere with the jaw excursions of a new patient.

The embodiments of the invention in which an exclusive property or privilege is claimed are defined as follows:

1. A vise for transfer of check-bites of a dental patient to a dental articulator comprising upper and lower center bearing plates carrying clutches fitting the patient's upper and lower arches and having forwardly extending exterior portions; upper and lower transverse bars having spherical ends secured between said ends to the respective exterior portions; the spherical ends of said lower transverse bar being spaced below the corresponding spherical ends of said upper transverse bar; and screw-actuated vise means spanning the corresponding ends of said bars for releasably frictionally gripping said spherical ends in any selected check-bite position of said plates and clutches.

2. The vise of claim 1 wherein each vise means comprises a pair of screw-actuated curved jaws which releasably frictionally grip said corresponding spherical ends therebetween.

3. The vise of claim 1 wherein said transverse bars carry cooperating tracing plate and styli means for recording jaw excursions for the respective check-bites.

4. The vise of claim 2 wherein each pair of jaws is screw-actuated by screw means thereacross between said corresponding spherical ends.

5. The vise of claim 4 wherein each pair of jaws has retaining means thereacross above the spherical end of said upper transverse bar to retain said jaws in downwardly depending relation for straddling the spherical end of said lower transverse bar.

6. The vise of claim 1 wherein one of said plates has a center bearing stud engaging the other one of said plates to space said plates apart a predetermined distance in all check-bite positions.

* * * * *